United States Patent
Hammerschmidt

(10) Patent No.: US 9,791,430 B2
(45) Date of Patent: Oct. 17, 2017

(54) MEASUREMENT OF TOTAL ORGANIC CARBON

(71) Applicant: HACH COMPANY, Loveland, CO (US)

(72) Inventor: Ramon Hammerschmidt, Peguera (ES)

(73) Assignee: HACH COMPANY, Loveland, CO (US)

( * ) Notice: Subject to any disclaimer, the term of this patent is extended or adjusted under 35 U.S.C. 154(b) by 0 days.

(21) Appl. No.: 14/721,960

(22) Filed: May 26, 2015

(65) Prior Publication Data

US 2016/0018376 A1 Jan. 21, 2016

Related U.S. Application Data

(60) Provisional application No. 62/002,651, filed on May 23, 2014.

(51) Int. Cl.
*G01N 33/18* (2006.01)
*G01N 21/35* (2014.01)
(Continued)

(52) U.S. Cl.
CPC ....... *G01N 33/1846* (2013.01); *G01N 21/272* (2013.01); *G01N 21/3504* (2013.01);
(Continued)

(58) Field of Classification Search
CPC .. G01N 21/272; G01N 21/35; G01N 21/3504; G01N 21/61; G01N 21/75;
(Continued)

(56) References Cited

U.S. PATENT DOCUMENTS

| | | | | |
|---|---|---|---|---|
| 3,051,603 A | * | 8/1962 | Michaels | C23G 1/02 134/28 |
| 3,639,514 A | * | 2/1972 | Schnalke et al. | C08F 255/02 525/244 |

(Continued)

FOREIGN PATENT DOCUMENTS

| | | | |
|---|---|---|---|
| CN | 102230881 A | * | 11/2011 |
| CN | 102565443 A | * | 7/2012 |
| FR | 1000938 | * | 2/1952 |

OTHER PUBLICATIONS

Sanchez-Gonzalez et al. Microchemical Journal, vol. 102, Dec. 9, 2011, pp. 75-82.*

(Continued)

*Primary Examiner* — Maureen Wallenhorst
(74) *Attorney, Agent, or Firm* — Samuel M. Freund; Cochran Freund & Young LLC

(57) ABSTRACT

A method for determining the total organic carbon in a sample which includes mixing the sample with a reagent containing at least one acid effective for reacting with inorganic carbon-containing materials in the sample, and at least one oxidizing agent effective for oxidizing organic carbon-containing materials in the sample in the presence of ultraviolet radiation, and detecting the carbon dioxide generated, is described. The at least one acid may include phosphoric acid, while the oxidizing agent may include sodium persulfate. In accordance with an embodiment of the inventive concept, the sample is first injected into a reaction chamber, which is continuously flushed with carbon dioxide free gas with no UV light present, and $CO_2$ generated from any inorganic carbon in the sample as carbonates is flowed through the detector, and may be recorded. Subsequent to this step, the UV light is passed through the reaction chamber and $CO_2$ generated from the reaction of the at least one oxidizing agent with the organic material in the solution (Continued)

in the presence of ultraviolet radiation, is flowed through the detector, which may be a non-dispersive infrared detector, after the reaction chamber is sparged using a carbon dioxide free gas, and recorded.

17 Claims, 3 Drawing Sheets

(51) Int. Cl.
  *G01N 21/71* (2006.01)
  *G01N 21/75* (2006.01)
  *G01N 21/3504* (2014.01)
  *G01N 21/27* (2006.01)
  *G01N 21/61* (2006.01)
(52) U.S. Cl.
  CPC .............. *G01N 21/75* (2013.01); *G01N 21/61* (2013.01); *Y10T 436/204998* (2015.01); *Y10T 436/235* (2015.01)
(58) Field of Classification Search
  CPC .............. G01N 33/1846; Y10T 436/10; Y10T 436/108331; Y10T 436/15; Y10T 436/153333; Y10T 436/156666; Y10T 436/16; Y10T 436/18; Y10T 436/182; Y10T 436/204998; Y10T 436/23; Y10T 436/235; Y10T 436/25; Y10T 436/25125; Y10T 436/25625; Y10T 436/25875
  USPC ...... 436/8, 18, 100, 101, 102, 103, 119, 120, 436/133, 145, 146, 164, 166, 174, 175, 436/179, 181; 252/408.1
  See application file for complete search history.

(56) References Cited

U.S. PATENT DOCUMENTS

| | | | |
|---|---|---|---|
| 4,277,438 A | 7/1981 | Ejzak | |
| 4,626,413 A | 12/1986 | Blades et al. | |
| 5,106,754 A | 4/1992 | Steele et al. | |
| 5,820,823 A * | 10/1998 | Godec | G01N 27/06 422/78 |
| 6,737,276 B1 * | 5/2004 | Voss | G01N 33/1846 422/145 |
| 2015/0111304 A1 * | 4/2015 | Leggett | G01N 33/1846 436/146 |

OTHER PUBLICATIONS

Seto et al. (abstract), Bunseki Kagaku, vol. 27(10), 1978, pp. 660-663.*

PCT International Search Report, Application No. PCT/US2015/032469, dated Aug. 14, 2015.

* cited by examiner

MEASUREMENT OF TOTAL ORGANIC CARBON

FIELD

Embodiments of the inventive concept relate generally to measurement of total organic carbon (TOC) in a water sample and, more particularly, to the measurement of TOC in a water sample using currently available UV/Persulfate TOC analyzers with a single solution of reagents.

BACKGROUND

Commercial Total Organic Carbon (TOC) analyzers are used to measure the quantity of organic carbon present in a water sample, which is an indicator of water purity. Applications for TOC measurements include ultrapure water for pharmaceutical and electronics manufacturing, as well as Municipal drinking water and wastewater and Industrial wastewater from chemical and petrochemical plants, as examples.

Measurement of TOC relies on the conversion or oxidation of organic material in a water sample to $CO_2$, which can then be measured by conductivity or Nondispersive Infrared (NDIR) detection, as examples. Two common methods of oxidation include UV/Persulfate and high-temperature combustion. The UV/Persulfate method uses the combination of ultraviolet light and strong chemical oxidants, for example, sodium persulfate, to convert organic material to $CO_2$. High-temperature combustion uses thermal oxidation processes, often in the presence of catalysts, to convert the organic materials to $CO_2$. Both methods use an acid, for example, phosphoric acid, to initially remove "Total Inorganic Carbon" or TIC present in the water sample, as $CO_2$, prior to the oxidation of the organic carbon. An example of a commercially available UV/Persulfate TOC analyzer is the GE/Sievers 900 Laboratory Analyzer, and an example of a high temperature combustion TOC analyzer is the Shimadzu TOC-L.

Chemical oxidants, acids, and dilution water are "reagents" consumed during TOC analyses, and can be expensive and difficult to handle for users of UV/Persulfate TOC analyzers. These reagents are purchased or prepared in separate containers at concentrations required by the manufacturers of TOC analysis equipment. In addition, currently available UV/Persulfate TOC analyzers require separate steps for the analysis, with each step designed to use one of the reagents. For example, the sample to be analyzed is often first diluted using added water to ensure that the sample TOC or TIC falls within the measurement range of the NDIR detector. Some commercial analyzers employ an "Autoranging" feature that automatically injects the correct dilution volume based on a preliminary measurement of the sample. An acid reagent is first added to react with the inorganic carbon compound in the sample to generate $CO_2$, followed by sparging the solution with a carbon dioxide free carrier gas, for example, purified oxygen or nitrogen, to remove the generated $CO_2$, which may be measured as TIC, or simply discarded. A chemical oxidant is then added to oxidize the organic carbon present in the sample to $CO_2$, generally with the aid of ultraviolet radiation. The $CO_2$ is again sparged from the solution using a carbon dioxide free gas, and measured yielding the Total Organic Carbon" or TOC. The sum of the TIC and TOC yields the Total Carbon, or TC, in the sample. Collectively, reagent preparation and/or handling along with these analysis steps comprise the reagent "workflow" required to measure TOC in a UV/Persulfate analyzer.

SUMMARY OF EMBODIMENTS OF THE INVENTIVE CONCEPT

An embodiment of the method for measuring organic carbon and/or total carbon in a sample, hereof, includes: mixing the sample with a reagent comprising an aqueous solution of both at least one acid effective for acidifying the resulting solution to a chosen pH value, whereby carbon dioxide from inorganic sources of carbon in the solution is generated, and at least one oxidizer effective for converting organic carbon into carbon dioxide only in the presence of ultraviolet radiation; sparging the resulting solution with a carbon dioxide free gas to remove carbon dioxide generated from inorganic carbon from the solution; irradiating the solution with ultraviolet light having a wavelength such that the at least one oxidizer converts organic carbon into carbon dioxide; sparging the resulting solution with a carbon dioxide free gas to remove carbon dioxide from organic carbon in the sample from the solution; and measuring the carbon dioxide removed from the solution by the second sparging step; whereby the total organic carbon in the solution is determined. The at least one acid may include at least one inorganic acid chosen from phosphoric acid, hydrochloric acid, nitric acid, and sulfuric acid, and mixtures thereof, while the at least one oxidizer may include a persulfate chosen from sodium persulfate and potassium Persulfate.

Benefits and advantages of embodiments of the inventive concept include, but are not limited to, providing a method for determining total organic carbon and/or total carbon in a sample, wherein all of the reagents consumed in a UV/Persulfate analysis of a sample are combined into a single, inexpensive and readily prepared reagent mixture having one blank to subtract to obtain accurate measurements, thereby reducing the reagent workflow and reagent costs.

BRIEF DESCRIPTION OF THE DRAWINGS

The accompanying drawings, which are incorporated in and form a part of the specification, illustrate the embodiments of the inventive concept and, together with the description, serve to explain the principles of the embodiments of the inventive concept. In the drawings.

DETAILED DESCRIPTION

Briefly, embodiments of the inventive concept include combining all the reagents consumed in a UV/Persulfate Total Carbon (TC) and/or Total Organic Carbon (TOC) analysis of a sample into one solution, thereby reducing the workflow and reagent costs. The present "mixed reagent" approach also simplifies the measurement calculations because there is only one blank TC or TOC value to subtract from subsequent measurements. This blank represents the TC or TOC originating from the acid and oxidant, as well as from the water used to prepare the reagent. With the use of individual reagents, as is currently taught by TC and TOC analysis apparatus manufacturers, TC or TOC blank values are separately determined for each reagent and subtracted from subsequent TC or TOC sample measurements. High-temperature combustion analyzers do not require chemical oxidants; therefore, the present mixed reagent approach might be used for the mixture of acid and dilution water.

Figure 1:
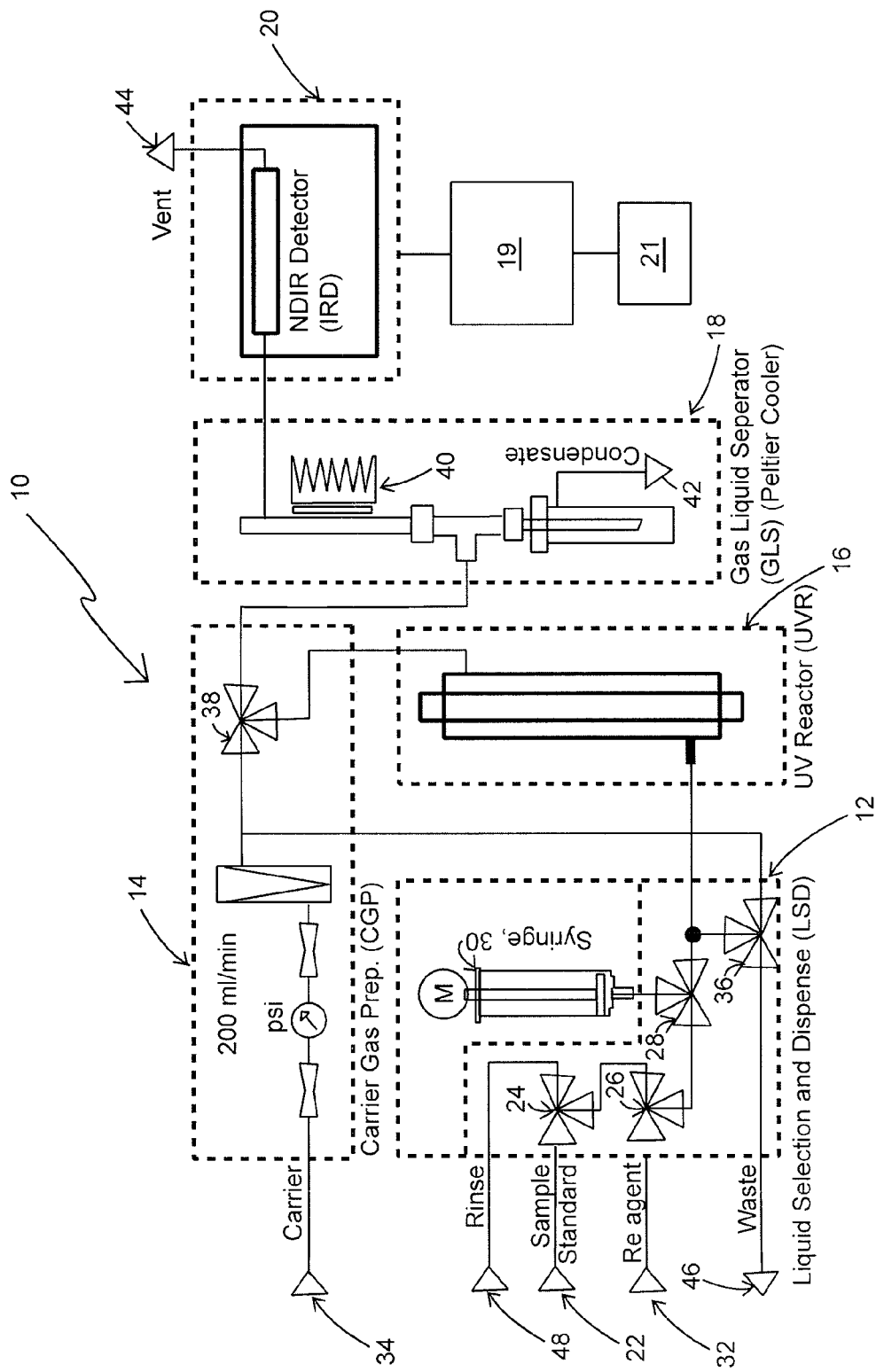
FIG. 1 is a schematic representation of an embodiment of an apparatus for performing embodiments of the method of the inventive concept.

Reference will now be made in detail to the embodiments of the inventive concept, examples of which are illustrated in the accompanying drawings. In the FIGURES, similar structure will be identified using identical reference characters. It will be understood that the FIGURES are for the purpose of describing particular embodiments of the inventive concept and are not intended to limit the inventive concept thereto. Turning now to FIG. 1, a schematic representation of an embodiment of apparatus, 10, for performing embodiments of the method of the inventive concept, hereof, illustrating liquid selection and dispensing apparatus, 12, carrier gas flow measurement and direction apparatus, 14, ultraviolet reactor, 16, gas/liquid separation apparatus, 18, and non-dispersive infrared detector, 20. Microprocessor, 19, controls the timing and functions of the elements of components 12, 14, 16, 18, and 20, of apparatus 10, as will be described in detail hereinbelow, and collects and processes the signals from NDIR detector 20 for display and recording, 21.

Liquid selection and dispensing apparatus 12 includes sample or standard, 22, introduced into three-way valve, 24, which directs the sample or standard to three-way valve, 26, and then to three-way valve, 28, where it can be drawn into motor-operated syringe, 30. Reagent, 32, is also introduced into valve, 26, from where it can be drawn into syringe 30. The mixed sample or standard and reagent are introduced into UV reactor 16 through three-way valve 28 by syringe 30. Carbon dioxide free carrier gas, 34, is directed through three-way valve, 36, with three-way valve, 38, blocking carrier gas flow otherwise, such that the mixed sample or standard and reagent is sparged in UV reactor 16. Carbon dioxide generated from inorganic carbon sources in the sample and entrained in the carrier gas may be directed through valve 38 into gas/liquid separator 18 out of UV reactor 16 into gas/liquid separator 18, where it is chilled using a Peltier, or other effective cooler, 40, to remove water, as condensate, 42, and directed into NDIR 20, for measurement, and venting, 44, or simply venting without measurement. With valve 38 permitting the flow of carrier gas through UV reactor 16, the UV irradiation source is activated. The UV irradiation source may include a mercury vapor lamp or an ultraviolet light emitting diode. Since the pH of the irradiated mixture is less than about 4, carbon dioxide generated from the organic carbon in the sample or standard is sparged through valve 38 and into gas/liquid separator 18 where water is removed therefrom using cooler 40, measured by NDIR detector 20, and vented through vent 44.

After each measurement, the irradiated mixture is withdrawn from UV reactor 16 by motorized syringe, 30, and expelled through valve 36 as waste liquid, 46. Reactor, 16, syringe 30, and valves 24, 26 and 28 may be rinsed using purified water, 48, drawn into syringe 30 through valves 24, 26 and 28.

When measuring a water sample to quantify TOC, most TOC analyzers add some combination of reagents and dilution water to the initial sample in order to complete the measurement. These added reagents and dilution water are potential sources of TOC that need to be subtracted from the final measurement result to obtain an accurate TOC value for the sample. As stated, embodiments of the apparatus and method of the present inventive concept combine at least one acid, at least one oxidizer, and dilution water into a single reagent, which makes this blank or background TOC subtraction more straightforward and ensures an accurate TOC measurement. Thus, measurements for TOC derive from two sources: (1) an unknown concentration of TOC in the sample; and (2) a small amount of background TOC that becomes known after a background measurement is taken.

NDIR 20 detects all $CO_2$ passing through it, a portion of this $CO_2$ may have originated from background carbon in the reagent. Background measurements may be made at the beginning of a run if there has not been a background measurement taken recently. Considering measuring a sample which has 100 ppb TOC, as an example, 8 mL of sample may be combined with 2 mL of reagent. The total measured $CO_2$ contains carbon that originated from both the sample and the reagent. The small concentration of carbon present in the 2 mL of reagent is subtracted and called "background". When the background is known, the calculations can be easily adjusted for the background based on how many milliliters of reagent are mixed with the sample. The reagent may be prepared by mixing 1 part of stock solution (composition hereof), for example containing approximately 1 molar sodium persulfate and approximately 1 molar phosphoric acid in water (250 g of $Na_2S_2O_8$ and 50 mL $H_3PO_4$ in 1 L DI $H_2O$ (high purity)), with 100 parts pure water (DI $H_2O$ (high purity). The background measurement is made using this reagent mixture.

Figure 2:
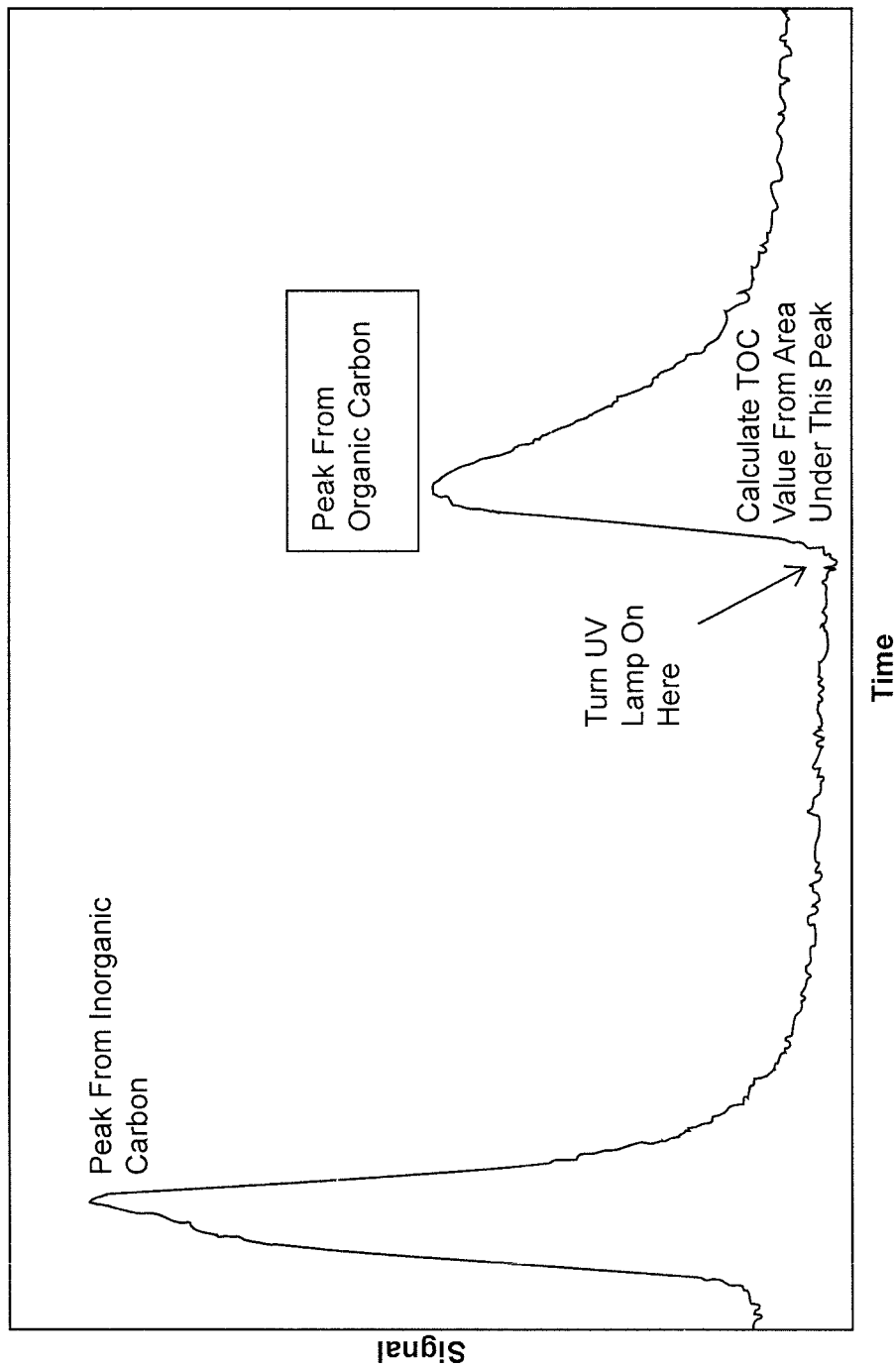
FIG. 2 is a graph of the measured signal as a function of time from a nondispersive infrared (NDIR) detector in accordance with the teachings of embodiments of the inventive concept.
Figure 3:
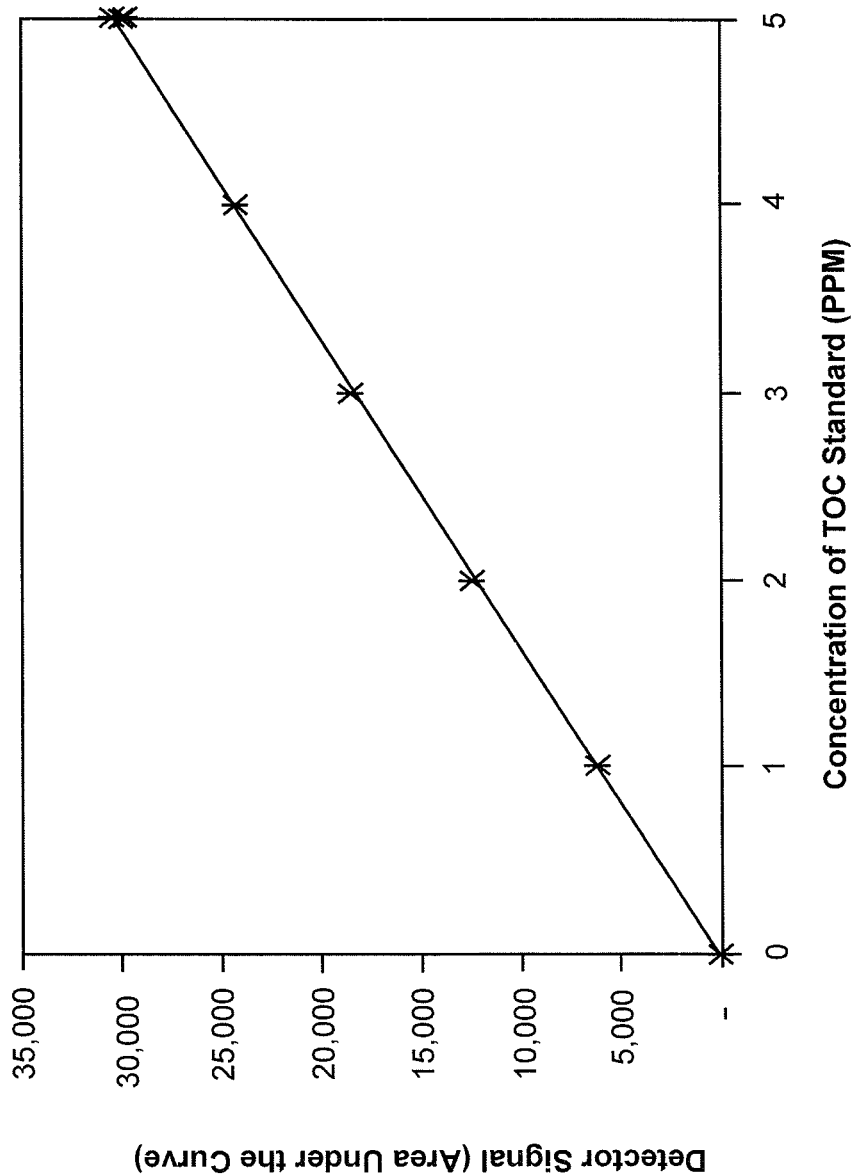
FIG. 3 is a calibration curve using the embodiment of the apparatus described in FIG. 1 hereof, where the area under the curve generated from a detected NDIR signal, an example of which is shown in FIG. 2, hereof, is plotted as a function of concentration of a standard solution.

Potassium hydrogen phthalate (KHP) may be used as the primary calibration standard. Calibration may be conducted by taking multiple measurements at different concentrations of a known primary standard. The area under the curve generated from a detected NDIR signal, an example of which is shown in FIG. 2, hereof, as a function of concentration of a standard solution, is shown in FIG. 3. Three repetitions each at concentrations 0 ppm (blank), 1 ppm, 2 ppm, 3 ppm, 4 ppm, and 5 ppm, were averaged to produce the calibration curve shown in FIG. 3.

A single 125 mL bottle of 5 ppm KHP has been found to suffice for such calibrations. Calibrations performed up to 5 ppm will cover the full measurement range (1 ppb-100 ppm), since samples containing greater than 5 ppm may be diluted less than 5 ppm. A reagent without added KHP standard may be measured for the blank values.

Having generally described embodiments of the inventive concept, the following EXAMPLE provides additional details.

EXAMPLE

A. Typical Operation of UV-Persulfate TOC Analyzers

Samples are diluted with water as required to fall within NDIR detector range, mixed with an acid, such as phosphoric acid, and injected into a reaction chamber. The acid converts inorganic carbonates into $CO_2$. After a chosen reaction period, as may be specified by the manufacturer, the chamber is sparged using an inert gas, such as nitrogen, driving the $CO_2$ gas from the chamber through the detector, where the level of inorganic carbon may be measured using standard NDIR techniques. When the inorganic carbon has been sparged, a reagent, such as sodium persulfate, is added to the reaction chamber, and UV radiation is passed through the chamber for oxidation of organic carbon. The flow of carbon-dioxide free gas is again flowed through to sparge the $CO_2$ gas from the solution and into the NDIR detector. This $CO_2$ is derived from organic carbon, and thus total organic carbon may be determined. In standard UV persulfate analyzers, pure water is typically used to dilute samples as needed.

B. Acid, Oxidizer, and Dilution Water Are Combined into a Single Reagent in Accordance with the Teachings of Embodiments of the Inventive Concept for Use in a Typical UV-persulfate TOC Analyzer In accordance with the teachings of embodiments of the present inventive concept, the sample is first diluted with reagent, which includes dilute phosphoric acid and sodium persulfate, as examples of the at least one acid and at least one oxidant, in water, as necessary to fall within NDIR detector range. For example, using a reagent mixture including approximately 0.01 molar sodium persulfate and approximately 0.01 molar phosphoric acid in water, a relatively high TOC sample (containing, for example, approximately 100 ppm of TOC), may be diluted such that the final mixture in the reaction vessel contains ~0.5 mL sample and ~9.5 mL of reagent. A lower TOC sample (containing, for example, approximately 100 ppb TOC) might not be significantly diluted, resulting in a final mixture in the reaction vessel with ~8 mL of sample and ~2 mL of reagent. The diluted sample is then injected into the reaction chamber, which is continuously sparged with inert gas with no ultraviolet radiation present, and $CO_2$ from any inorganic carbon in the sample may be passed through the NDIR detector, and recorded. Subsequent to this step, the UV radiation is directed into the sample and $CO_2$ from the organic carbon is generated for 5 min., as an example, flowed through the NDIR detector, and recorded. The reagent blank is determined by running a measurement with only reagent, which determines how much TOC is present in the reagent.

Before the next sample is analyzed, the fluid lines of the analyzer are backwards flushed with the reagent mixture, and that back flush is emptied to a waste container.

It should be mentioned that the inert gas acts as a carrier to transport the $CO_2$ from the reaction chamber to the NDIR detector. The NDIR detector measures the $CO_2$ signal as illustrated in FIG. 2. The area under the curve is then calculated by integration. This area may be converted (from Volt-seconds) to a meaningful TOC value by use of a calibration curve stored in the microprocessor. The calibration procedure is standard, using a primary calibration standard to measure known concentrations of TOC. The area-under-the curve measurements for the known concentrations are used to create a calibration curve, which is used to determine TOC values when measuring (unknown) samples.

The foregoing description of embodiments of the inventive concept has been presented for purposes of illustration and description and is not intended to be exhaustive or to limit embodiments of the inventive concept to the precise form disclosed, and obviously many modifications and variations are possible in light of the above teaching. The embodiments were chosen and described in order to best explain the principles of the inventive concept and its practical application to thereby enable others skilled in the art to best utilize embodiments of the inventive concept in various embodiments and with various modifications as are suited to the particular use contemplated. It is intended that the scope of embodiments of the inventive concept be defined by the claims appended hereto.

| FIGURE LEGEND |
| --- |
| 10: Measurement Apparatus |
| 12: Liquid Selection and Dispensing Apparatus |
| 14: Carrier Gas Flow Measurement and Direction Apparatus |
| 16: Ultraviolet Reactor |
| 18: Gas/Liquid Separation Apparatus |
| 20: Nondispersive Infrared Detector |
| 22: Sample or Standard Source |
| 24: Three-Way Valve |
| 26: Three-Way Valve |
| 28: Three-Way Valve |
| 30: Motor-Operated Syringe |
| 32: Reagent Source |
| 34: Carrier Gas Source |
| 36: Three-Way Valve |
| 38: Three-Way Valve |
| 40: Cooler |
| 42: Condensate |
| 44: Gas Venting Outlet |
| 46: Waste Liquid |
| 48: Source of Purified Rinse Water |

What is claimed is:

1. A method for measuring total organic carbon in a sample, comprising: in a reaction chamber, mixing the sample with a reagent comprising an aqueous solution of both at least one acid effective for acidifying the sample-reagent solution formed thereby to a chosen pH value, whereby carbon dioxide from inorganic sources of carbon in the solution is generated, and at least one oxidizer effective for converting organic carbon into carbon dioxide only in the presence of ultraviolet radiation; sparging the resulting solution with a carbon dioxide free gas to remove carbon dioxide generated from inorganic carbon from the solution; irradiating the solution in the reaction chamber with ultraviolet light having a wavelength such that the at least one oxidizer converts organic carbon into carbon dioxide; sparging the resulting solution with a carbon dioxide free gas to remove carbon dioxide from organic carbon in the sample from the solution; and measuring the carbon dioxide removed from the solution by the second sparging step; whereby the total organic carbon in the solution is determined.

2. The method of claim 1, wherein the carbon dioxide is measured using non-dispersive infrared detection having a range of detection for carbon dioxide.

3. The method of claim 2, further comprising the step of removing water from the carbon dioxide before said step of measuring the carbon dioxide.

4. The method of claim 2, further comprising the step of diluting the sample using the reagent if the carbon dioxide generated from the sample is greater than the range for carbon dioxide detection.

5. The method of claim 1, further comprising the step of measuring the carbon dioxide removed from the solution by said step of sparging before said step of irradiating the solution, whereby total inorganic carbon may be determined.

6. The method of claim 5, further comprising the step of removing water from the carbon dioxide before said step of measuring the carbon dioxide.

7. The method of claim 6, wherein the carbon dioxide is measured using non-dispersive infrared detection.

8. The method of claim 6, wherein total carbon is determined as the sum of the total inorganic carbon and the total organic carbon in the sample.

9. The method of claim 1, wherein the acid comprises at least one inorganic acid.

10. The method of claim 9, wherein the at least one inorganic acid is chosen from phosphoric acid, hydrochloric acid, nitric acid, and sulfuric acid, and mixtures thereof.

11. The method of claim 1, wherein the at least one oxidizer comprises a persulfate.

12. The method of claim 11, wherein the persulfate is chosen from sodium persulfate and potassium persulfate.

13. The method of claim 1, wherein the carbon dioxide free gas is chosen from oxygen and nitrogen.

14. The method of claim 1, wherein the step of irradiating the solution is undertaken for less than or equal to about 5 min., followed by the step of sparging the irradiated solution.

15. The method of claim 1, wherein the step of irradiating the solution is performed using an irradiation source chosen from a mercury vapor lamp, and an ultraviolet light emitting diode.

16. The method of claim 1, wherein the chosen pH value is less than about 4.

17. The method of claim 1, wherein the reagent comprises about 0.01 molar phosphoric acid and about 0.01 molar persulfate in water.

* * * * *